(12) United States Patent
Wynne et al.

(10) Patent No.: US 12,035,966 B2
(45) Date of Patent: Jul. 16, 2024

(54) LASER-ASSISTED TREATMENT OF PACHYONYCHIA CONGENITA

(71) Applicant: International Business Machines Corporation, Armonk, NY (US)

(72) Inventors: James J. Wynne, Mount Kisco, NY (US); Jerome M. Felsenstein, Pleasantville, NY (US); Robert S. Olyha, Jr., LaGrange, NY (US)

(73) Assignee: International Business Machines Corporation, Armonk, NY (US)

( * ) Notice: Subject to any disclaimer, the term of this patent is extended or adjusted under 35 U.S.C. 154(b) by 395 days.

(21) Appl. No.: 16/888,693

(22) Filed: May 30, 2020

(65) Prior Publication Data

US 2021/0369346 A1 Dec. 2, 2021

(51) Int. Cl.
*A61B 18/20* (2006.01)
*A61B 5/00* (2006.01)
*A61B 18/00* (2006.01)
*G01N 29/24* (2006.01)

(52) U.S. Cl.
CPC ............ *A61B 18/20* (2013.01); *A61B 5/0095* (2013.01); *G01N 29/2418* (2013.01); *A61B 2018/00452* (2013.01); *A61B 2018/00577* (2013.01); *A61B 2018/00642* (2013.01); *A61B 2018/00904* (2013.01)

(58) Field of Classification Search
None
See application file for complete search history.

(56) References Cited

U.S. PATENT DOCUMENTS

| 4,504,727 | A | 3/1985 | Melcher et al. |
| 4,784,135 | A | 11/1988 | Blum et al. |
| 6,165,170 | A | 12/2000 | Wynne et al. |
| 6,447,503 | B1 | 9/2002 | Wynne et al. |
| 6,694,173 | B1* | 2/2004 | Bende ............... A61B 5/0095 601/3 |
| 10,413,359 | B2 | 9/2019 | Felsenstein et al. |
| 10,456,197 | B2 | 10/2019 | Felsenstein et al. |
| 2008/0108942 | A1 | 5/2008 | Brister et al. |
| 2008/0114428 | A1* | 5/2008 | Trembly ............. A61B 18/20 607/100 |
| 2013/0190742 | A1 | 7/2013 | Connors et al. |
| 2015/0025444 | A1 | 1/2015 | Felsenstein et al. |
| 2015/0025445 | A1 | 1/2015 | Felsenstein et al. |
| 2016/0324569 | A1* | 11/2016 | Hoitink ............. A61B 18/1206 |
| 2017/0325835 | A1 | 11/2017 | Bowe et al. |
| 2018/0098807 | A1 | 4/2018 | Schwartz |
| 2020/0246179 | A1* | 8/2020 | Peyman ............... A61K 9/51 |
| 2021/0169559 | A1* | 6/2021 | Li ........................ A61B 18/20 |

FOREIGN PATENT DOCUMENTS

EP 1286634 B1 3/2003

\* cited by examiner

*Primary Examiner* — Sean W Collins
*Assistant Examiner* — Nora W Rhodes
(74) *Attorney, Agent, or Firm* — Daniel Morris; Otterstedt & Kammer PLLC (57) ABSTRACT

A method for controlled ablation of target tissue includes activating laser ablation of hyperkeratotic tissue upon detecting a trigger input signal, detecting a photo-acoustical signature due to the laser ablation of the hyperkeratotic tissue, detecting a change in the photo-acoustical signature due to the laser ablation of a material different than the hyperkeratotic tissue, and ceasing the laser ablation upon detecting, by a signal processor, the change in the photo-acoustical signature.

15 Claims, 4 Drawing Sheets

LASER-ASSISTED TREATMENT OF PACHYONYCHIA CONGENITA

BACKGROUND

Pachyonychia Congenita (PC) is a genetic autosomal dominant skin disorder. PC is believed to be caused by a mutation in one of five keratin genes KRT6A, KRT6B, KRT6C, KRT16 or KRT17. Keratin genes are responsible for production of keratins, which are tough, fibrous proteins that form filaments to support skin cells and give them shape and strength, helping the skin cells handle pressure and stretching. With PC, the filaments do not form properly, resulting in abnormal keratin production of the nails, palms, soles, and intraoral cavity. Abnormal keratin production can be associated with significant painful disabilities.

Current treatments with drugs show effectiveness, but with significant side effects.

Rapamycin (also known as sirolimus), administered orally, has been shown to inhibit the translation of K6a mRNA.16. In a human proof of concept study with a small number of PC patients with either PC-K6a or PC-K16 (related to the affected keratin gene where the mutation is located), oral rapamycin demonstrated promising efficacy results, with all patients in the study reporting reduced pain levels and improved life quality as measured by the validated Dermatology Quality of Life Index instrument. However, common adverse reactions observed with rapamycin include peripheral edema, hypercholesterolemia, abdominal pain, headache, nausea, diarrhea, chest pain, stomatitis, nasopharyngitis, acne, upper respiratory tract infection, dizziness, and myalgia. Oral rapamycin treatment may additionally increase the risk of type 2 diabetes. These well-known side effects of oral rapamycin led to the early withdrawal of all patients from the study. The results from this human proof of concept study suggest that the development of a topical version of rapamycin with high local concentrations and minimal systemic absorption may be a viable therapeutic option for PC.

Small interfering RNA (siRNA) is a class of RNA molecules. This class of RNA molecules is known to interfere with the expression of specific genes with complementary nucleotide sequences by degrading mRNA after transcription, preventing translation. siRNA is an effective local therapy, altering the genetic mutation causing PC. However, local introduction by current methods can cause intolerable pain.

BRIEF SUMMARY

According to one or more embodiments of the present invention, a method for controlled ablation of target tissue includes activating a laser ablation of hyperkeratotic tissue upon detecting a trigger input signal, detecting a photo-acoustical signature due to the laser ablation of the hyperkeratotic tissue, detecting a change in the photo-acoustical signature due to the laser ablation of a material different than the hyperkeratotic tissue, and ceasing the laser ablation upon detecting, by a signal processor, the change in the photo-acoustical signature.

According to some embodiments of the present invention, a system comprises a microphone, a pre-amplifier connected to an output of the microphone, a high-pass filter connected to an output of the pre-amplifier, a comparator connected to an output of the high-pass filter, and a digital signal processor receiving a signal output from the comparator, wherein the digital signal processor outputs a first signal to control a gain of the pre-amplifier and a second signal used by the comparator to compare against a photo-acoustical signature captured by the microphone, and wherein the digital signal processor enables a laser ablation of a target material based on the photo-acoustical signature associated with laser ablation of the target material.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. For example, one or more embodiments provide one or more of:

An improved system and method for removing tissue using laser ablation;

An improved system and method for removing tissue in a controlled and sterile way using laser ablation;

An improved system and method for removing tissue using laser ablation with precise endpoint termination;

An improved system and method for removing tissue using laser ablation with a precise, self-terminated endpoint;

An improved system and method for removing tissue using laser ablation, where the removed tissue is a thick hyperkeratotic layer overlying moist, viable skin;

An improved system and method for removing tissue using a laser emitting short pulses of far ultraviolet (far-UV) 193 nm wavelength (6.4 eV photon energy) light, being preferably an argon fluoride (ArF) pulsed excimer laser;

An improved system and method for removing tissue using laser ablation to create transdermal orifices through the hyperkeratotic layer caused by PC, ceasing tissue removal when exposed to (i) hydrated tissue containing aqueous chloride ions from tissue fluids, e.g., blood, lymph, plasma, or (ii) a saline solution-filled blister, enabling transdermal medication to be introduced painlessly through these orifices with great precision; and An improved system and method for removing tissue using laser ablation to create transdermal orifices through the hyperkeratotic layer caused by PC, enabling transdermal medication to be introduced painlessly in these orifices, encased in biodegradable hydrogels or in nanoparticulate form, for sustained release or immediate penetration.

These and other features and advantages of the present invention will become apparent from the following detailed description of illustrative embodiments thereof, which is to be read in connection with the accompanying drawings.

BRIEF DESCRIPTION OF THE SEVERAL VIEWS OF THE DRAWINGS

Preferred embodiments of the present invention will be described below in more detail, with reference to the accompanying drawings.

DETAILED DESCRIPTION

Pachyonychia Congenita (PC) is a genetic autosomal dominant skin disorder. PC is caused by a mutation in genes responsible for production of keratins. Keratins are tough, fibrous proteins that form filaments to support skin cells and give them shape and strength, helping these skin cells handle pressure and stretching. With PC, the filaments do not form properly resulting in abnormal keratin production of the nails, palms, soles, and intraoral cavity, and a hyperkeratotic layer of external tissue that can result in significant painful disabilities.

Current treatments of PC with drugs show effectiveness, but with significant side effects. In particular, transdermal introduction of medication is excruciatingly painful, often requiring anesthesia.

According to an embodiment of the present disclosure, a method of penetrating dry keratin (e.g., on the soles of the feet) includes irradiating the keratin with a pulsed argon fluoride (ArF) excimer laser to create orifices terminating when the underlying moist, vascular tissue or saline solution-filled blisters are unveiled, which enables the painless introduction of rapamycin, siRNA, or other therapeutic drugs through the orifices to the underlying tissue.

Some embodiments of the present invention utilize an ArF excimer laser, which emits short pulses of far ultraviolet radiation, to create transdermal orifices through the hyperkeratotic layer. Tissue removal is ceased upon exposure of (i) hydrated tissue containing aqueous chloride ions from tissue fluids, e.g., blood, lymph, plasma, or (ii) a saline solution filled blister. According to one or more embodiments, transdermal medication is introduced through these orifices. Such application can be precise and painless. According to some embodiments, the medication can be encased in biodegradable hydrogels or in nanoparticulate form, for immediate penetration or sustained release.

Laser ablation of tissue is a process wherein the laser radiation is absorbed in a layer less than approximately 10 micrometers (um) at the surface of the tissue. The wavelength for such strong absorption is in the ultraviolet region of the electromagnetic spectrum. This absorption converts the long chain protein molecules of the tissue into smaller, more volatile fragments, which are ejected from the surface, carrying away substantially all of the deposited laser energy in a plume composed of small tissue fragments down to the molecular level, as well as water vapor and other gases. Such ablation constitutes tissue removal with minimal thermal damage to the underlying and adjacent tissue, while destroying any remaining infectious agents, eliminating the sources of infection.

According to an embodiment of the present disclosure, viable tissue differs from hyperkeratotic tissue, the aqueous chloride ions in viable tissue are a strong absorber of ultraviolet radiation at wavelengths below about 200 nanometers (nm), with an absorption maximum at 190 nm. Thus, the salt water that is a major component of viable tissue will block the incoming UV light and completely halt the ablation process.

According to an embodiment of the present disclosure, the laser beam is terminated or moved to another location when the hyperkeratotic layer is fully perforated at a current location. According to some embodiments, the signal to terminate the irradiation, upon complete penetration through the hyperkeratotic layer at a particular location, is derived by detecting a change in a photo-acoustic signature from each laser pulse, generated by the ablated tissue that is converted to a gas that is rapidly expelled into the air. There is a significant burst of sound with each laser pulse while keratin is being ablated. This sound is substantially diminished upon complete penetration of the keratin layer, because the aqueous chloride ions in the exposed hydrated tissue or saline solution-filled blisters absorb the laser radiation by electron photo-detachment, a non-thermal process that does not result in the production of sound.

Current treatments of pachyonychia congenita, by transdermal introduction of medication, can be painful, often requiring anesthesia. Methods according to embodiments of the present invention are more precise, at least due to the determination/control of the depth of medication delivery. Creating transdermal orifices through the hyperkeratotic layer, according to some embodiments, is less painful (or painless), and the delivery of medication through these orifices will also be painless.

Figure 1:
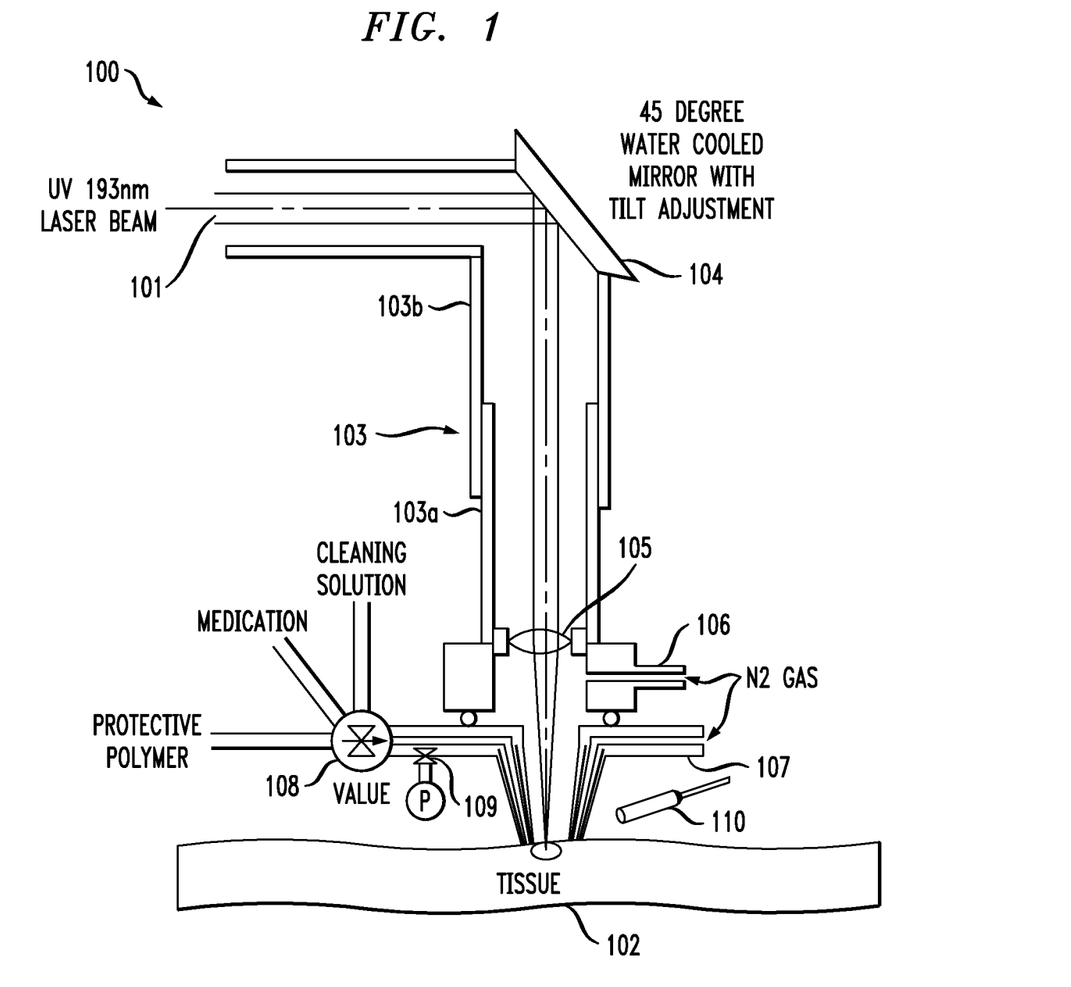
FIG. 1 is a diagram of an excimer laser beam tissue ablation system configured according to exemplary embodiments of the present invention.

FIG. 1 is a cross-sectional view of a system according to some embodiments of the present invention. The system 100 comprises an ArF excimer laser (not shown) producing a laser beam 101. The laser beam 101 is guided to a target (e.g., tissue 102) through an enclosed channel 103. According to some embodiments, the channel 103 includes a 45-degree water cooled mirror 104 and a lens 105 focusing the laser beam 101 on the target. According to at least one embodiment, the mirror has a tilt adjustment feature. The system 100 includes inlets 106-107 providing $N_2$ gas to the channel 103 and the target. According to some embodiments, the $N_2$ gas flowing through inlet 106 protects the lens 105 and clears away debris that may result from the plume of material ablated from the tissue 102. This gas also fills the channel 103 to eliminate oxygen that would absorb some of the laser beam energy. According to some embodiments, the length of the channel 103 is adjustable by sliding a smaller diameter laser beam exit section 103a within a larger diameter laser beam entry section 103b. According to one or more embodiments, the $N_2$ gas flowing through inlet 107 cleans a transdermal orifice as it is being created by laser ablation in the tissue 102. The system 100 includes an inlet controlled by a valve 108 for providing a cleaning solution, dispensing medication, and/or dispensing a protective polymer to the target, depending on a position of a valve 108. According to some embodiments, the protective polymer may be a hydrogel that prevents the medication from diffusing out of the transdermal orifice. According to some embodiments, a purging source of gas or liquid P, controlled by a valve 109, can be used to clean the inlet between the valve 108 and the inlet exit at the tissue 102. According to some embodiments, the system 100 includes a microphone 110, recording the sounds produced by ablation, which are used to determine when to turn the laser off and/or move to a next target (e.g., upon determining that the hyperkeratotic tissue has been removed based on a decrease in a photo-acoustical signature associated with an unveiling of moist viable tissue or saline solution).

According to some embodiments of the present invention, in an improved system and method for removing tissue using laser ablation, the completion of the laser-created orifice through the hyperkeratotic layer is determined by detecting a change of a photo-acoustic signature. According to one or more embodiments, a significant burst of sound is produced with each laser pulse while keratin is being ablated. The sound is generated by the ablated tissue that is converted to a gas and rapidly expelled into the air. The sound is detectably diminished or absent when the laser radiation falls on moist viable tissue or saline solution. Embodiments of the present invention use the detection of change in sound to trigger cessation of the laser ablation or to move the target location of the laser to a new area of tissue.

According to some embodiments of the present invention, in an improved system and method for removing tissue using laser ablation, the completion of the laser-created orifice through the hyperkeratotic layer is determined by detecting a change of a photo-acoustic signature using a microphone 110. A signal output by the microphone 110 is analysed, and upon determining an appropriate change in the photo-acoustic signature, e.g., greater than a threshold or within a range associated with moist viable tissue or saline solution, the system shuts off the laser or directs the laser beam to a new location on the hyperkeratotic tissue to initiate the creation of a new orifice.

According to one or more embodiments, the laser emits short-pulse, far ultraviolet (far-UV) at about 193 nm wavelength (about 6.4 eV photon energy) light. The laser is a preferably an argon fluoride (ArF) pulsed excimer laser. Using this wavelength has the result of being self-terminating when viable tissue or saline solution-filled blisters are exposed. Therefore, the laser ablation termination point occurs automatically. In this way, the irradiated thick hyperkeratotic layer can be removed with minimal or no collateral damage to the adjacent or underlying viable tissue, because once the radiation from the laser contacts the viable tissue or saline solution, the ablation process terminates (e.g., even before the laser is disabled).

Figure 2:
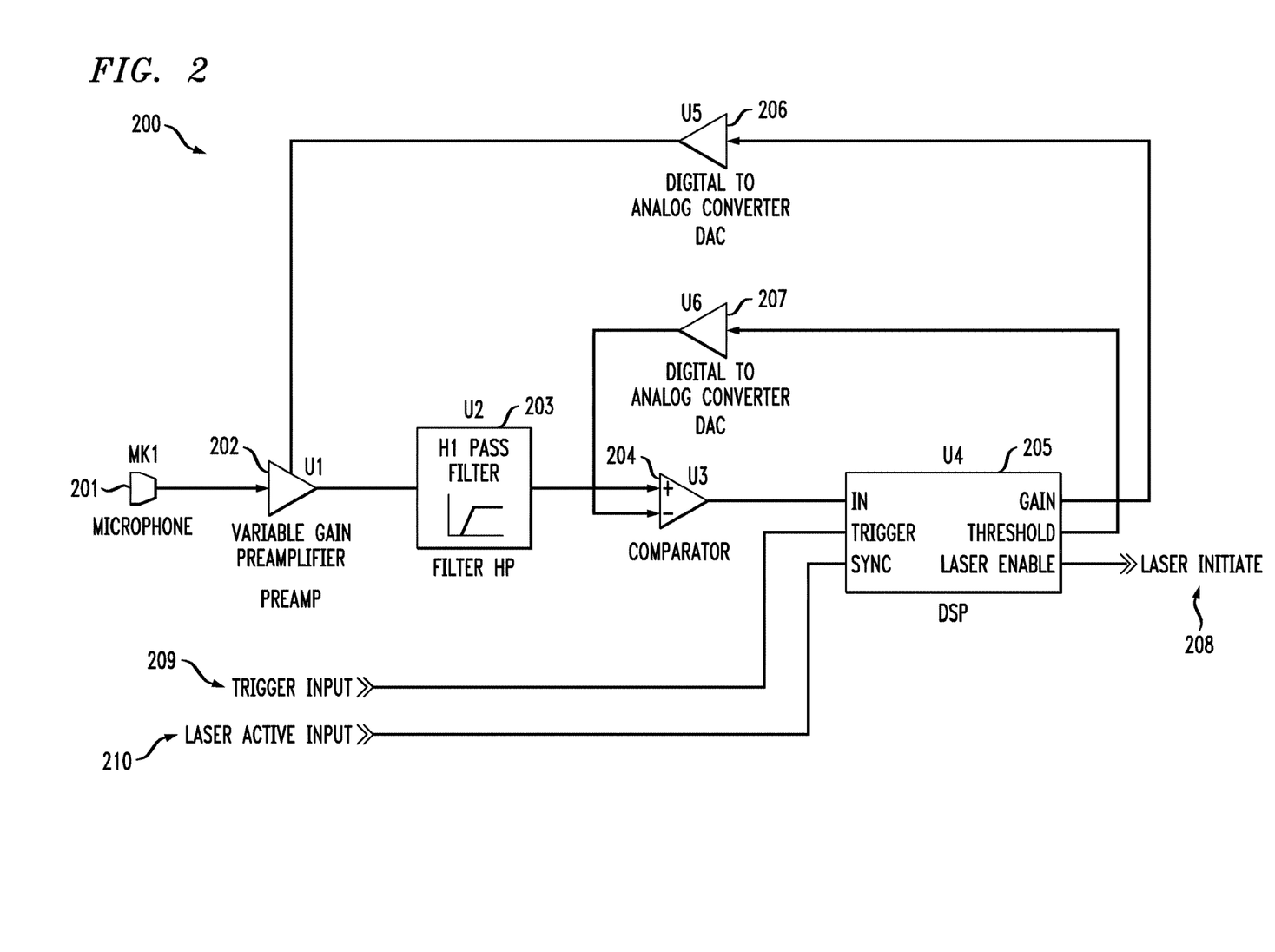
FIG. 2 is a block diagram of a photo-acoustic detection system configured to control laser ablation according to an exemplary embodiment of the present invention.

Referring to FIG. 2, a system 200 according to one or more embodiments, comprises a microphone 201, a preamplifier (preamp) 202 connected to an output of the microphone 201, a filter 203 (e.g., a high-pass (HP) filter) connected to an output of the preamp 202, a comparator 204 connected to an output of the filter 203, and a digital signal processor (DSP) 205. The DSP 205 receives a signal output from the comparator 204, and a trigger input 209 and a laser active input 210. The DSP 205 outputs signals including a gain signal to a first digital-to-analog converter (DAC) 206 and a threshold signal to a second DAC 207. The first DAC 206 outputs a signal to the preamp 202. The second DAC 207 outputs a signal to the comparator 204.

The system 200 uses the microphone 201 to detect the presence and absence of photo-acoustic signals associated with laser ablation of target materials (e.g., hyperkeratotic layer of skin) and control the operation of a laser through an output port, laser enable, of the DSP 205 and a laser initiate signal 208.

Figure 3:
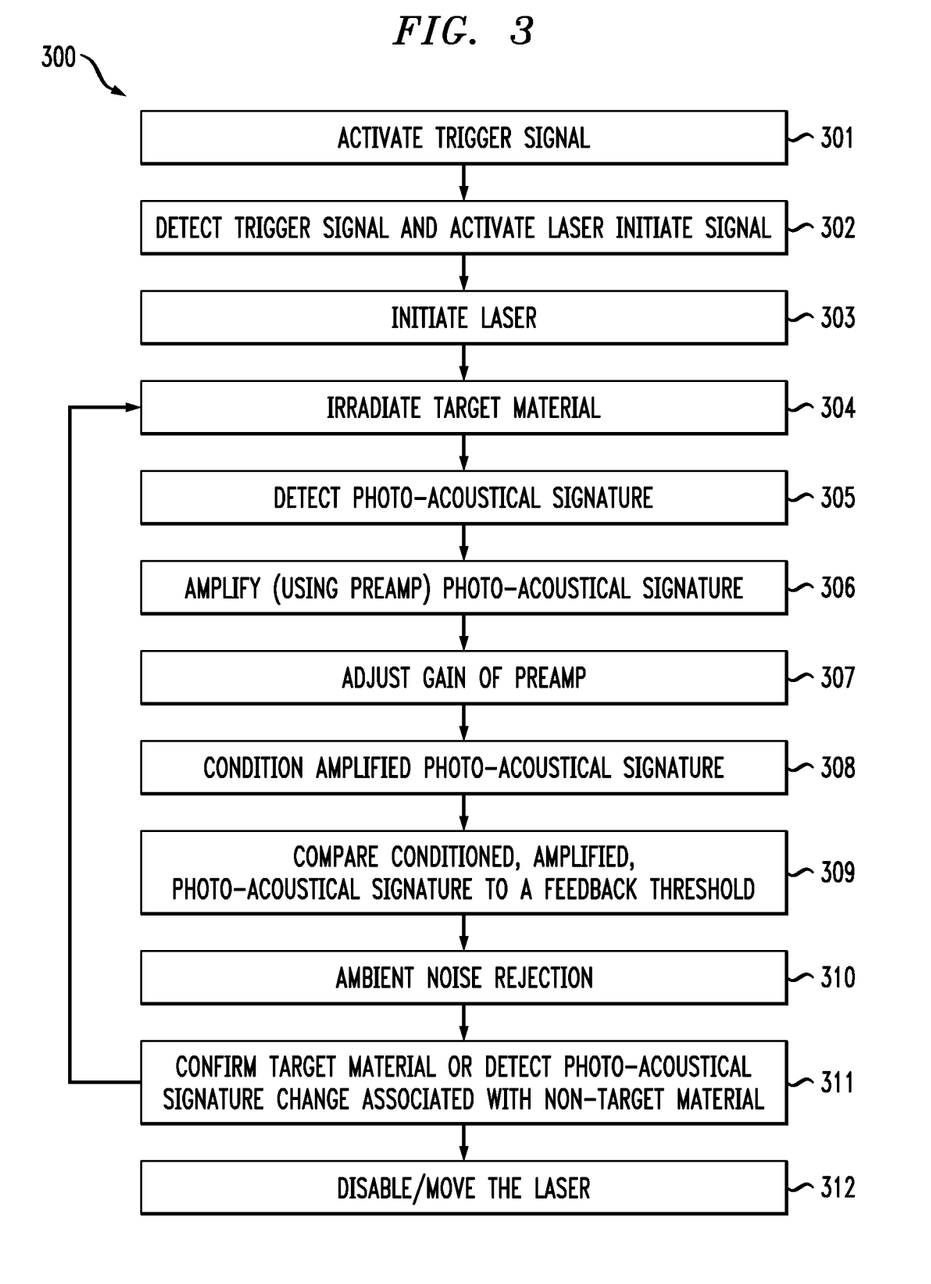
FIG. 3 is a flow diagram of a method according to some embodiments of the present invention.

Referring to FIG. 3, according to some embodiments, a method 300 performed by the system includes an operator activating a trigger input signal 209 to start a laser sequencer at 301. According to some embodiments, the laser sequencer is a computer-controlled armature, stepper, etc., controlling the application of the laser to a target or sequence of targets. The DSP 205 detects the trigger input signal and activates the laser initiate signal 208 at 302. The laser initiate signal 208 is output to a laser controller (not shown), which causes the laser to emit short pulses (about 10-20 nanoseconds (nsec) in duration) of far-UV radiation at a repetition rate of about 10-50 pulses per second at 303. The target material is then exposed to the laser pulses 304, causing a photo-acoustical signature response from the target, a burst of sound with each laser pulse. The photo-acoustical signature response is detected by the microphone 201 at 305. The microphone output is amplified by the preamp 202 at 306. The gain of the preamp 203 can be adjusted by the DSP 205 in conjunction with the first DAC 206 to increase the signal level to a usable value and/or to compensate for differing photo-acoustical signature responses at 307. A high pass filter 203 further conditions the signal and reduces effects of low frequency ambient noise at 308. A comparator 204 compares the acoustical signal output by the filter 203 to a feedback threshold signal generated by the DSP 205 and the second DAC 207 in a feedback loop. The comparator 204 outputs a digital signal of logic level, 0 or 1, depending on whether the conditioned acoustical signal is less than or greater than the second DAC output at 309.

The output signal of the comparator 204 is a signal present on the IN input port of the DSP 205, which is active only when the laser is irradiating the target material at 311. That is, the laser remains engaged while target material is being ablated and disengages upon determining that the target material has been removed. According to some embodiments, ambient noise rejection can optionally be improved by using the laser active input signal 210, which the DSP 205 can use to correlate with the microphone input at 310. Once the photo-acoustical signature is initially detected, the DSP 205 will continue to analyze the photo-acoustical data and detect when the signature changes or ceases 311, at which point the DSP 205 will disable the laser initiate signal, stopping the laser at 312. The method then returns to block 301 and waits for a new trigger event.

According to some embodiments, in a case of a programmed laser sequencer/stepper, the system can move the laser beam to a next position and continuing ablating the target tissue in a new area at 312.

Recapitulation:

According to one or more embodiments of the present invention, a method for controlled ablation of target tissue includes activating a laser ablation of hyperkeratotic tissue upon detecting a trigger input signal (303), detecting a photo-acoustic signature due to the laser ablation of the hyperkeratotic tissue (305), detecting a change in the photo-acoustical signature due to the laser ablation of a material different than the hyperkeratotic tissue (311), and ceasing the laser ablation upon detecting, by a signal processor, the change in the photo-acoustical signature (312).

According to some embodiments of the present invention, a system (200) comprises a microphone (201), a pre-amplifier (202) connected to an output of the microphone, a high-pass filter (203) connected to an output of the pre-amplifier, a comparator (204) connected to an output of the high-pass filter, and a digital signal processor (205) receiving a signal output from the comparator, wherein the digital signal processor outputs a first signal to control a gain of the pre-amplifier and a second signal used by the comparator to compare against a photo-acoustical signature captured by the microphone, and wherein the digital signal processor enables a laser ablation of a target material based on the photo-acoustical signature associated with laser ablation of the target material.

Furthermore, it should be noted that any of the methods described herein can include an additional step of providing a computer system implementing a method for controlled ablation of target (e.g., hyperkeratotic) tissue. Further, a computer program product can include a tangible computer-readable recordable storage medium with code adapted to be executed to carry out one or more method steps described herein, including the provision of the system with the distinct software modules.

Figure 4:
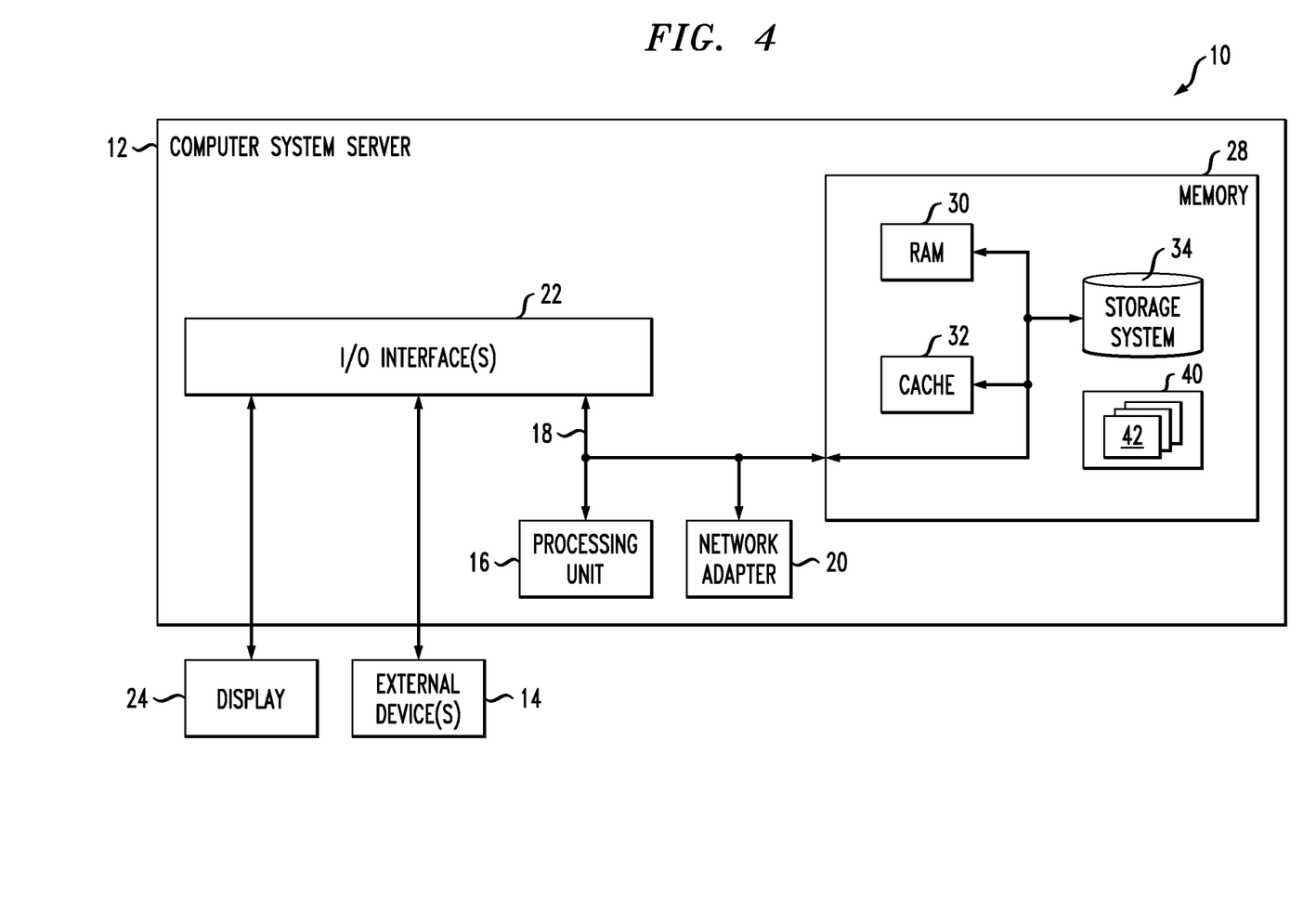
FIG. 4 is a block diagram depicting an exemplary computer system configured for controlling laser ablation according to an exemplary embodiment of the present invention.

One or more embodiments of the invention, or elements thereof, can be implemented in the form of an apparatus including a memory and at least one processor that is coupled to the memory and operative to perform exemplary method steps. FIG. 4 depicts a computer system/server 12 that may be useful in implementing one or more aspects and/or elements of the system 10 (e.g., see system 200, FIG. 2).

The computer system/server 12 is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types.

As shown in FIG. 4, computer system/server 12 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc.

Thus, one or more embodiments can make use of software running on a general purpose computer or workstation. With reference to FIG. 4, such an implementation might employ, for example, a processor 16, a memory 28, and an input/output interface 22 to a display 24 and external device(s) 14 such as a keyboard, a pointing device, or the like. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 4) running a server program. It will be understood that such a physical server may or may not include a display and keyboard.

It should be noted that any of the methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described. The method steps can then be carried out using the distinct software modules and/or sub-modules of the system, as described above, executing on one or more hardware processors such as 16. Further, a computer program product can include a computer-readable storage medium with code adapted to be implemented to carry out one or more method steps described herein, including the provision of the system with the distinct software modules.

One example of user interface that could be employed in some cases is hypertext markup language (HTML) code served out by a server or the like, to a browser of a computing device of a user. The HTML is parsed by the browser on the user's computing device to create a graphical user interface (GUI).

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for controlled ablation of target tissue comprising:
    activating a laser ablation of hyperkeratotic tissue upon detecting a trigger input signal;
    detecting a photo-acoustical signature due to the laser ablation of the hyperkeratotic tissue;
    detecting a change in the photo-acoustical signature due to the laser ablation of a material different than the hyperkeratotic tissue; and
    ceasing the laser ablation upon detecting, by a signal processor, the change in the photo-acoustical signature, wherein the laser ablation remains engaged while the hyperkeratotic tissue is being ablated and disengages upon determining that the hyperkeratotic tissue has been removed and wherein the determination that the hyperkeratotic tissue has been removed is based on a detection of a gas that is rapidly expelled as a result of the generation of the ablated tissue, the detection of the gas being based on the change in the photo-acoustical signature.

2. The method of claim 1, wherein the photo-acoustical signature is captured by a microphone.

3. The method of claim 2, further comprising:
    generating, by a preamplifier, an amplified version of the photo-acoustical signature captured by the microphone; and
    adjusting a gain of the preamplifier based on a first feedback response generated by the signal processor.

4. The method of claim 2, further comprising conditioning, by a high pass filter, the photo-acoustical signature.

5. The method of claim 2, further comprising rejecting ambient noise captured by the microphone by using a laser active input signal, which the signal processor correlates with the photo-acoustical signature.

6. The method of claim 1, further comprising comparing, by a comparator, the photo-acoustical signature to a second feedback response generated by the signal processor, wherein the second feedback response is a threshold, and wherein the detection of the photo-acoustical signature due to the laser ablation of the hyperkeratotic tissue is based on the comparison.

7. The method of claim 1, wherein the determination that the hyperkeratotic tissue has been removed is based on a decrease in a photo-acoustical signature associated with an unveiling of moist viable tissue or saline solution.

8. The method of claim 1, the activating the laser ablation further comprising emitting ultraviolet light at a wavelength of about 193 nm with a photon energy of about 6.4 eV to automatically trigger termination of an ablation of the hyperkeratotic tissue.

9. A non-transitory computer readable medium comprising computer executable instructions which when executed by a computer system cause the computer to perform the method for controlled ablation of target tissue, the method comprising:
   activating a laser ablation of hyperkeratotic tissue upon detecting a trigger input signal;
   detecting a photo-acoustical signature due to the laser ablation of the hyperkeratotic tissue;
   detecting a change in the photo-acoustical signature due to the laser ablation of a material different than the hyperkeratotic tissue; and
   ceasing the laser ablation upon detecting, by a signal processor, the change in the photo-acoustical signature, wherein the laser ablation remains engaged while the hyperkeratotic tissue is being ablated and disengages upon determining that the hyperkeratotic tissue has been removed and wherein the determination that the hyperkeratotic tissue has been removed is based on a detection of a gas that is rapidly expelled as a result of the generation of the ablated tissue, the detection of the gas being based on the change in the photo-acoustical signature.

10. The computer readable medium of claim 9, wherein the photo-acoustical signature is captured by a microphone.

11. The computer readable medium of claim 10, further comprising:
   generating, by a preamplifier, an amplified version of the photo-acoustical signature captured by the microphone; and
   adjusting a gain of the preamplifier based on a first feedback response generated by the signal processor.

12. The computer readable medium of claim 10, further comprising conditioning, by a high pass filter, the photo-acoustical signature.

13. The computer readable medium of claim 10, further comprising rejecting ambient noise captured by the microphone by using a laser active input signal, which the signal processor correlates with the photo-acoustical signature.

14. The computer readable medium of claim 9, further comprising comparing, by a comparator, the photo-acoustical signature to a second feedback response generated by the signal processor, wherein the second feedback response is a threshold, and wherein the detection of the photo-acoustical signature due to the laser ablation of the hyperkeratotic tissue is based on the comparison.

15. The computer readable medium of claim 14, wherein the determination that the hyperkeratotic tissue has been removed is based on a decrease in a photo-acoustical signature associated with an unveiling of moist viable tissue or saline solution.

* * * * *